United States Patent
Kane et al.

(10) Patent No.: US 11,344,224 B2
(45) Date of Patent: May 31, 2022

(54) DETECTION OF RESPIRATORY DISORDERS

(71) Applicant: KONINKLIJKE PHILIPS N.V., Eindhoven (NL)

(72) Inventors: Michael Thomas Kane, Harrison City, PA (US); Sankarasubrahmani Uday Shankar, Chennai (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 395 days.

(21) Appl. No.: 14/652,800

(22) PCT Filed: Dec. 9, 2013

(86) PCT No.: PCT/IB2013/060743
§ 371 (c)(1),
(2) Date: Jun. 17, 2015

(87) PCT Pub. No.: WO2014/097047
PCT Pub. Date: Jun. 26, 2014

(65) Prior Publication Data
US 2015/0320338 A1 Nov. 12, 2015

Related U.S. Application Data

(60) Provisional application No. 61/739,084, filed on Dec. 19, 2012.

(51) Int. Cl.
*A61B 5/08* (2006.01)
*A61B 5/00* (2006.01)
(Continued)

(52) U.S. Cl.
CPC .......... *A61B 5/0826* (2013.01); *A61B 5/085* (2013.01); *A61B 5/4818* (2013.01);
(Continued)

(58) Field of Classification Search
CPC ........ A61B 5/085; A61B 5/0826; A61B 5/08; A61B 5/053; A61B 5/0809; A61M 2016/0027; A61M 2230/46
See application file for complete search history.

(56) References Cited

U.S. PATENT DOCUMENTS 6,066,101 A * 5/2000 Johnson ................. A61B 5/085
600/529
6,210,345 B1 * 4/2001 Van Brunt ........... A61H 9/0078
600/529
(Continued)

FOREIGN PATENT DOCUMENTS

JP 2012523262 A 10/2012
WO WO 2011067698 A2 * 6/2011 ............. A61B 5/085

OTHER PUBLICATIONS

E. Oostveen, The forced oscillation technique in clinical practice: methodology, recommendations and future developments, 2003, European Respiratory Journal, 22, pp. 1026-1041.*
(Continued)

*Primary Examiner* — Daniel L Cerioni
*Assistant Examiner* — Raymond P Dulman (57) ABSTRACT

Systems and methods for monitoring pulmonary edema and/or pulmonary congestion are based on changes in impedance parameters that are indicative of lung impedance of a patient. Early detection of changes in the status of a patient pertaining to pulmonary edema and/or pulmonary congestion may be especially beneficial for heart failure patients. Quantification is based on differentials, e.g. within a span of 24 hours, of one or more lung impedance parameters.

8 Claims, 2 Drawing Sheets

(51) Int. Cl.
*A61B 5/085* (2006.01)
*A61M 16/00* (2006.01)

(52) U.S. Cl.
CPC ......... *A61M 16/026* (2017.08); *A61B 5/4848* (2013.01); *A61M 2016/0027* (2013.01); *A61M 2016/0039* (2013.01); *A61M 2016/0042* (2013.01); *A61M 2205/332* (2013.01); *A61M 2205/3306* (2013.01); *A61M 2205/3317* (2013.01); *A61M 2230/46* (2013.01); *A61M 2230/63* (2013.01)

(56) References Cited

U.S. PATENT DOCUMENTS

| | | | |
|---|---|---|---|
| 6,257,234 B1 * | 7/2001 | Sun | A61M 16/026 128/204.18 |
| 6,435,182 B1 * | 8/2002 | Lutchen | A61M 16/026 128/204.21 |
| 7,325,545 B2 | 2/2008 | Dellaca | |
| 7,575,553 B2 | 8/2009 | Stahmann | |
| 7,704,215 B2 | 4/2010 | Lewicke | |
| 8,002,553 B2 | 8/2011 | Hatlestad | |
| 8,070,686 B2 | 12/2011 | Belalcazar | |
| 8,821,404 B2 * | 9/2014 | Thakur | A61B 5/0538 600/508 |
| 2001/0004893 A1 | 6/2001 | Biondi | |
| 2002/0078957 A1 * | 6/2002 | Remmers | A61M 16/00 128/204.18 |
| 2003/0159695 A1 | 8/2003 | Younes | |
| 2005/0080461 A1 | 4/2005 | Stahmann | |
| 2005/0115561 A1 * | 6/2005 | Stahmann | A61B 5/0031 128/200.24 |
| 2005/0142070 A1 | 6/2005 | Hartley | |
| 2006/0169282 A1 * | 8/2006 | Izumi | A61B 5/08 128/204.18 |
| 2008/0091114 A1 * | 4/2008 | Min | A61B 5/0537 600/508 |
| 2008/0139956 A1 * | 6/2008 | Diong | A61B 5/085 600/533 |
| 2009/0312649 A1 | 12/2009 | Lian | |
| 2010/0113890 A1 | 5/2010 | Cho | |
| 2010/0198097 A1 | 8/2010 | Sowelam | |
| 2010/0307487 A1 | 12/2010 | Dunsmore | |
| 2012/0022388 A1 | 1/2012 | Pittman | |
| 2013/0150747 A1 * | 6/2013 | Pompilio | A61B 5/085 600/533 |

OTHER PUBLICATIONS

Vaskar Mukerji, Dyspnea, Orthopnea, and Paroxysmal Noctournal Dyspnea, 1990, Clinical Methods: The History, Physical, and Laboratory Examinations, Butterworths, 3rd Edition, pp. 78-80.*

Dai Yumino, Noctrunal Rostral Fluid Shift a Unifying Concept for the Pathogenesis of Obstructive and Central Sleep Apnea in Men With Heart Failure, Apr. 12, 2010, Circulation, vol. 121, Issue 14, pp. 1598-1605.*

Alexandre Duguet, Expiratory flow limitation as a determinant of orthopnea in acute left heart failure, 2000, Journal of the American College of Cardiology, vol. 35, Issue 3, pp. 690-700 (Year: 2000).*

Black, et al., Airway resistance and tissue elastance from input or transfer impedance in bronchoconstricted monkeys, 2001, Journal of Applied Physiology, 90, p. 571-578 (Year: 2001).*

Yumino Dai et al., "Nocturnal Rostral Fluid Shift : A Unifying Concept for the Pathogenesis of Obstructive and Central Sleep Apnea in Men With Heart Failure", Circulation 2010 Journal of the American Heart Association, http://circ.ahajournals.org/content/121/14/1598.

* cited by examiner

DETECTION OF RESPIRATORY DISORDERS

CROSS-REFERENCE TO RELATED APPLICATIONS

This patent application claims the priority benefit under 35 U.S.C. § 371 of international patent application no. PCT/IB2013/060743, filed Dec. 9, 2013, which claims the priority benefit under 35 U.S.C. § 119(e) of U.S. Provisional Application No. 61/739,084 filed on Dec. 19, 2012, the contents of which are herein incorporated by reference.

BACKGROUND OF THE INVENTION

1. Field of the Invention

The present disclosure pertains to systems and methods to monitor respiratory disorders, and, in particular, to monitor such disorders based on changes in measurements is a respiratory parameter taken before and after sleeping.

2. Description of the Related Art

Respiratory conditions and/or diseases are related to a person's general health and/or wellbeing. Certain respiratory conditions, including but not limited to pulmonary edema, airway inflammation, and/or pulmonary congestion, may need to be monitored for certain patients, including but not limited to heart failure patients. Respiratory conditions such as these are both prevalent and medically undesirable.

SUMMARY OF THE INVENTION

Accordingly, one or more embodiments provide a system to monitor a lung parameter, such as pulmonary edema, airway resistance and/or pulmonary congestion. The system comprises a pressure generator configured to generate a pressurized flow of breathable gas for delivery to a subject, one or more sensors configured to generate one or more output signals conveying information related to one or more gas parameters of the pressurized flow of breathable gas, and one or more processors configured to execute computer program modules. The computer program modules comprises a control module configured to control the pressure generator to adjust one or more levels of the one or more gas parameters of the pressurized flow of breathable gas. A parameter determination module is configured to determine an airway parameter. The parameter determination module is configured to determine a monitoring parameter that reflects a change between a first measurement of the respiratory parameter and a second measurement of the respiratory parameter. The first measurement is taken prior to the second measurement, and the timing of the first measurement and the second measurement, e.g. with respect to a sleeping session of the subject, results in a change and/or allows for an observed change in the respiratory parameter between the first measurement and the second measurement. A detection module is configured to quantify a characteristic of a lung of the subject based on the monitoring parameter.

It is yet another aspect of one or more embodiments to provide a method for monitoring pulmonary edema and/or pulmonary congestion. The method comprises generating a pressurized flow of breathable gas for delivery to the airway of a subject, generating one or more output signals conveying information related to one or more gas parameters of the pressurized flow of breathable gas, adjusting one or more levels of the one or more gas parameters of the pressurized flow of breathable gas, determining a first measurement of a respiratory parameter of the subject, wherein the first measurement is based on the one or more generated output signals, determining a second measurement of the respiratory parameter, wherein the second measurement is based on the one or more generated output signals, wherein the first measurement is taken prior to the second measurement, wherein the timing of the first measurement and the second measurement, e.g. with respect to a sleeping session of the subject, results in a change and/or allows for an observed change in the respiratory parameter between the first measurement and the second measurement, determining a monitoring parameter that reflects the change between the first measurement and the second measurement, and detecting, monitoring, and/or quantifying a characteristic of the lung of the subject based on the monitoring parameter.

It is yet another aspect of one or more embodiments to provide a system configured to monitor pulmonary edema and/or pulmonary congestion. The system comprises means for generating a pressurized flow of breathable gas for delivery to the airway of a subject; means for generating one or more output signals conveying information related to one or more gas parameters of the pressurized flow of breathable gas; means for adjusting one or more levels of the one or more gas parameters of the pressurized flow of breathable gas; means for determining a first measurement of a respiratory parameter of the subject, wherein the first measurement is based on the one or more generated output signals; means for determining a second measurement of the respiratory parameter, wherein the second measurement is based on the one or more generated output signals, wherein the first measurement is taken prior to the second measurement, wherein the second measurement is based on the one or more generated output signals, and wherein the timing of the first measurement and the second measurement results in a change and/or allows for an observed change in the respiratory parameter between the first measurement and the second measurement; means for determining a monitoring parameter that reflects the change between the first measurement and the second measurement; and means for detecting, monitoring, and/or quantifying a characteristic of the lung of the subject based on the monitoring parameter.

These and other aspects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
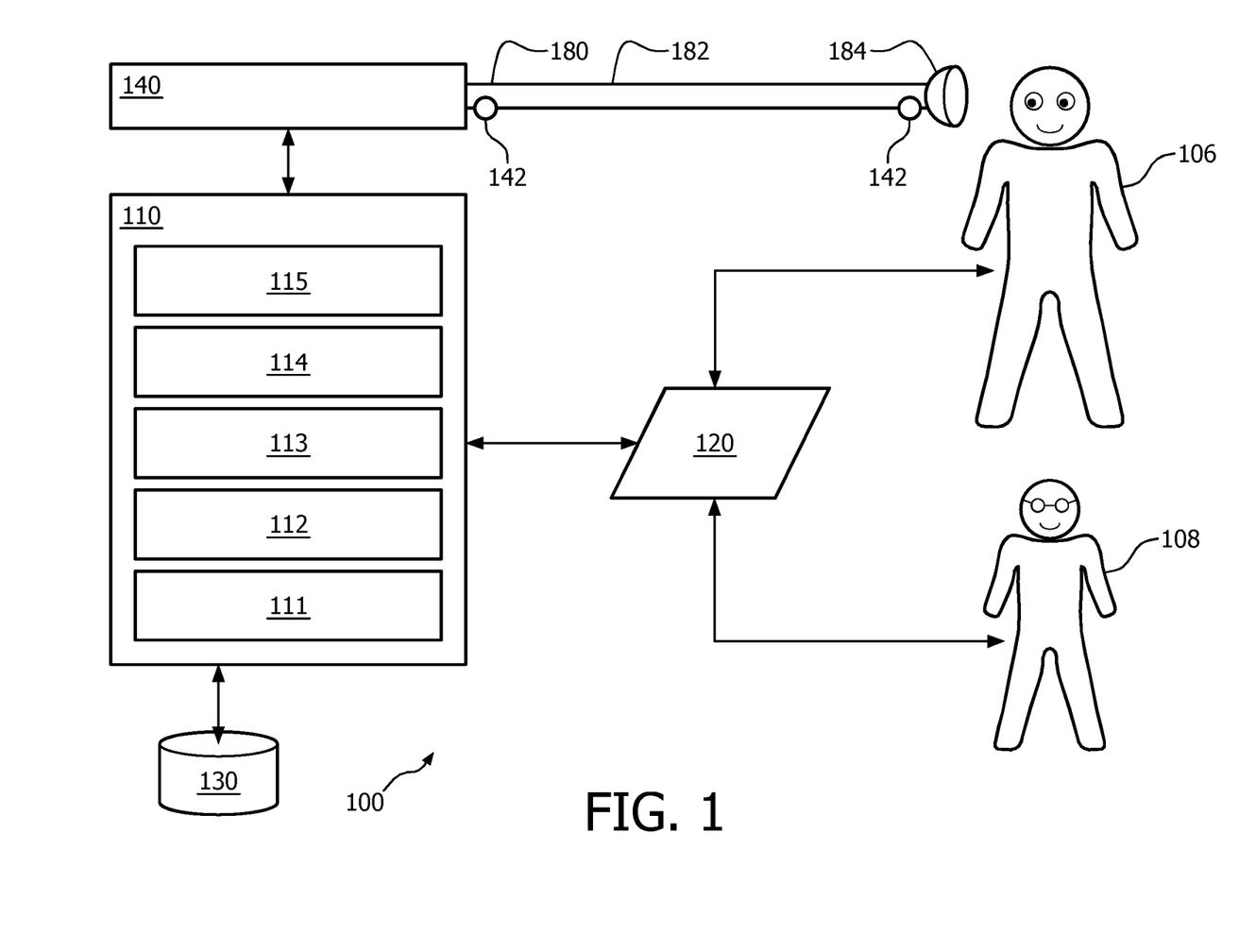
FIG. 1 schematically illustrates a system to monitor pulmonary edema and/or pulmonary congestion, according to one or more embodiments.

FIG. 1 schematically illustrates a system 100 to monitor pulmonary edema and/or pulmonary congestion. System 100 includes one or more of a pressure generator 140, a delivery circuit 180, one or more sensors 142, one or more processors 110, a control module 111, a parameter determination module 112, a detection module 113, a trending module 114, a perturbation module 115, an electronic storage 130, a user interface 120, and/or other components and/or computer program modules.

Heart Failure includes symptoms caused by cardiac failure which include Volume Overload, an increase in extracellular fluid and blood volume, and/or other symptoms. Volume overload may result in peripheral edema and cardiogenic pulmonary edema. A portion of heart failure patients may also be impacted by some form of sleep disordered breathing (SDB). Rostral fluid shift is nocturnal fluid shift into the neck, nares, and/or other tissue which may increase tissue volume. Rostral fluid shift among heart failure patients may contribute to obstructed SDB and the accumulation of pulmonary fluid during sleep. Excess pulmonary fluid results in pulmonary edema and/or pulmonary congestion. Pulmonary congestion pertains to excess fluid which remains within the extracellular space. Worsening conditions will result in pulmonary edema when fluid begins to accumulate in ventilated air passages. In contrast, excess pulmonary fluid may be dispersed during the (subsequent) day time and/or waking period. Acute Decompensated Heart Failure (ADHF) patients may be especially affected by increased interstitial fluid and/or blood plasma levels, as well as (respiratory) conditions including, but not limited to, pulmonary edema and/or pulmonary congestion. Asthma is a disorder that causes the airways of the lungs to swell and narrow, leading to wheezing, shortness of breath, chest tightness, and coughing.

Patients for whom pulmonary congestion is a symptomatic response to ADHF may benefit from monitoring, quantifying, and/or detection of, e.g., pulmonary edema and/or pulmonary congestion. Patients suffering from asthma may benefit from monitoring changes in airway resistance. Patients with Chronic Obstructive Pulmonary Disease may benefit from monitoring changes in obstructive lung symptoms. Monitoring of such respiratory parameters may involve an analysis of measurements indicating airway and/or lung impedance and/or resistance and/or airway and/or lung reactance of a subject, changes therein within one or more days, changes in and around the alveoli of the subject, and/or trends in measurements and/or changes over one or more days. In some embodiments, the one or more measurements are taken using a pressurized flow of breathable gas that is generated by pressure generator 140.

Pressure generator 140 of system 100 in FIG. 1 may be integrated, combined, coupled, and/or connected with a (positive) airway pressure device (PAP/CPAP/BiPAP®/ etc.). Pressure generator 140 is configured to provide a pressurized flow of breathable gas for delivery to the airway of subject 106, e.g. via delivery circuit 180. Delivery circuit 180 may interchangeably be referred to as subject interface 180. Subject 106 is not required to but may initiate one or more phases of respiration. Respiratory therapy may be implemented as CPAP, pressure control, pressure support, volume control, and/or other types of support and/or control. For example, to support inspiration, the pressure of the pressurized flow of breathable gas may be adjusted to an inspiratory pressure. Alternatively, and/or simultaneously, to support expiration, the pressure and/or flow of the pressurized flow of breathable gas may be adjusted to an expiratory pressure. Adjustments may be made numerous times in implementations using auto-titrating for providing respiratory support through the delivery of the pressurized flow of breathable gas.

In addition to alternating between multiple levels, the inhalation pressure level may ramp up or down according to a predetermined slope (absolute and/or relative, e.g. dependent on breathing rate) for any specified section of a phase. Similar features may be available for exhalation phases. The pressure levels may be predetermined and fixed, follow a predetermined dynamic characteristic, or they may dynamically change breath-to-breath or night-to-night depending on sensed breathing, breathing disorder, or other physiological characteristics. Pressure generator 140 is configured to adjust one or more of pressure levels, flow, humidity, velocity, acceleration, and/or other parameters of the pressurized flow of breathable gas, e.g. in substantial synchronization with the breathing cycle of the subject.

An airway pressure device may be configured such that one or more gas parameters of the pressurized flow of breathable gas are controlled. The airway pressure device may operate in accordance with a therapeutic respiratory regimen for subject 106. The one or more gas parameters include one or more of flow, volume, retrograde volume, pressure, humidity, velocity, acceleration, (intentional) gas leak, and/or other parameters. System 100 may be configured to provide types of therapy including types of therapy where a subject performs inspiration and/or expiration of his own accord. In some embodiments, an airway pressure device may be configured to provide negative airway pressure.

The pressurized flow of breathable gas is delivered from pressure generator 140 to the airway of subject 106 via delivery circuit 180. Delivery circuit 180 may include a conduit 182 and/or a subject interface appliance 184. Conduit 182 may include a flexible length of hose, or other conduit, either in single-limb or dual-limb configuration that places subject interface appliance 184 in fluid communication with pressure generator 140. Conduit 182 forms a flow path through which the pressurized flow of breathable gas is communicated between subject interface appliance 184 and pressure generator 140. Conduit 182 may comprise a standard 22 mm diameter hose (other common diameters range between ¾" and 1") or, in certain embodiments, a much smaller diameter hose that is in the range of ⅓ the diameter of a standard size hose. Such a hose may be referred to as a restricted flow hose or limited flow hose. Such a hose may for example have a diameter ranging between ¼" and ⅓", or alternatively between 6 mm and 9 mm. Such a hose may have a greater resistance to gas flow.

Subject interface appliance 184 of system 100 in FIG. 1 is configured to deliver the pressurized flow of breathable gas to the airway of subject 106. As such, subject interface appliance 184 may include any appliance suitable for this function. In some embodiments, pressure generator 140 is a dedicated ventilation device and subject interface appliance 184 is configured to be removably coupled with another interface appliance being used to deliver respiratory therapy to subject 106. For example, subject interface appliance 184 may be configured to engage with and/or be inserted into an endotracheal tube, a tracheotomy portal, and/or other interface appliances. In one embodiment, subject interface appliance 184 is configured to engage the airway of subject 106 without an intervening appliance. In this embodiment, subject interface appliance 184 may include one or more of an endotracheal tube, a nasal cannula, a tracheotomy tube, a nasal mask, a nasal/oral mask, a full-face mask, a total facemask, and/or other interface appliances that communicate a flow of gas with an airway of a subject. The present disclosure is not limited to these examples, and contemplates delivery of the pressurized flow of breathable gas to subject 106 using any subject interface.

One or more sensors 142 of system 100 in FIG. 1 are configured to generate output signals conveying information related to one or more gas parameters of the pressurized flow of breathable gas. In some embodiments, one or more sensors 142 are configured to generate output signals conveying information related to one or more physiological parameters and/or respiratory parameters.

The one or more sensors 142 may include one or more of a pressure sensor, flow sensor, flow meter, gas meter, current sensor, accelerometer, positional sensor, movement sensor, light sensor, infra-red (IR) sensor, electromagnetic sensor, electrode, tilt meter, (video) camera, and/or other sensors. The illustration of sensor 142 including two members in FIG. 1 is not intended to be limiting. In some embodiments, system 100 uses one sensor or more than two sensors. The illustration of the locations of sensors 142 as depicted in FIG. 1 is not intended to be limiting. An individual sensor 142 may be located at or near pressure generator 140, at or near subject interface appliance 184, at or near (a body part of) subject 106, embedded and/or integrated in subject interface appliance 184, and/or at other locations. Resulting signals or information from one or more sensors 142 are transmitted to one or more of processor 110, user interface 120, electronic storage 130, and/or other components of system 100. This transmission may be wired and/or wireless.

The one or more sensors 142 are configured to generate output signals in an ongoing manner, e.g. before, during, and/or after a period of rest and/or sleep. As used herein, the term "sleep" may refer to any period of resting, regardless of the state of wakefulness. As used herein any period of sleep may be referred to interchangeably as a "sleep period," "sleeping period," or "sleep session." As used herein, the term "waiting period" may refer to a period long enough for a subject's lung impedance to measurably change, e.g. one or more minutes, about half an hour, one or more hours, part of a day, and/or other suitable waiting periods. Generating output signals may include generating signals intermittently, periodically (e.g. at a sampling rate), continuously, continually, at varying intervals, and/or in other ways that are ongoing. The sampling rate may be about 1 μs, about 1 ms, about 0.01 second, about 0.1 second, about 1 second, about 10 seconds, about 1 minute, and/or other sampling rates.

In some embodiments, the one or more sensors 142 may be configured to generate output signals that pertain to a measurement during a measurement period. The measurement period may be about 1 second, about 1 minute, about 3 minutes, and/or other measurement periods. During measurement periods, the sampling rates may be as described above. Measurement periods may be repeated about hourly, every few hours, twice a day, a few times per day, before and/or after a sleeping and/or resting period, and/or at any other suitable interval for the purposes described herein. It is noted that multiple individual sensors 142 may operate using different sampling rates, as appropriate for the particular output signals and/or (frequencies related to particular) parameters derived therefrom.

In some embodiments, the generated output signals may be considered as a vector of output signals, such that a vector includes multiple samples of information conveyed related to one or more parameters. Different parameters may be related to different vectors, and vice versa. A particular parameter determined in an ongoing manner from a vector of output signals may be considered as a vector of that particular parameter.

Referring to FIG. 1, electronic storage 130 of system 100 comprises electronic storage media that electronically stores information. The electronic storage media of electronic storage 130 may include one or both of system storage that is provided integrally (i.e., substantially non-removable) with system 100 and/or removable storage that is removably connectable to system 100 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 100 to function properly. For example, electronic storage 130 may record or store vectors of parameters based on the generated output signals, and/or other parameters (as discussed elsewhere herein), and/or other information. Electronic storage 130 may be a separate component within system 100, or electronic storage 130 may be provided integrally with one or more other components of system 100 (e.g., processor 110).

User interface 120 of system 100 in FIG. 1 is configured to provide an interface between system 100 and a user (e.g., a user 108, subject 106, a caregiver, a therapy decision-maker, etc.) through which the user can provide information to and receive information from system 100. This enables data, results, and/or instructions and any other communicable items, collectively referred to as "information," to be communicated between the user and system 100. An example of information that may be conveyed by user 108 to system 100 is patient-specific or subject-specific information related to a level of inspiratory pressure to be used for the pressurized flow of breathable gas. An example of information that may be conveyed to user 108 is a report detailing measurements of lung impedance spanning multiple days during a period of monitoring subject 106. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 100 from removable storage (e.g., a smart card, a flash drive, a removable disk, etc.) that enables the user(s) to customize system 100. Other exemplary input devices and techniques adapted for use with system 100 as user interface 120 include, but are not limited to, an RS-232 port, radio-frequency (RF) link, an infra-red (IR) link, modem (telephone, cable, Ethernet, internet or other). In short, any technique for communicating information with system 100 is contemplated as user interface 120.

Processor 110 of system 100 in FIG. 1 is configured to provide information processing capabilities in system 100. As such, processor 110 includes one or more of a digital processor, an analog processor, a digital circuit designed to process information, an analog circuit designed to process information, and/or other mechanisms for electronically processing information. Although processor 110 is shown in FIG. 1 as a single entity, this is for illustrative purposes only. In some embodiments, processor 110 includes a plurality of processing units.

As is shown in FIG. 1, processor 110 is configured to execute one or more computer program modules. The one or more computer program modules include one or more of control module 111, parameter determination module 112, detection module 113, trending module 114, perturbation module 115, and/or other modules. Processor 110 may be configured to execute modules 111-115 by software; hardware; firmware; some combination of software, hardware, and/or firmware; and/or other mechanisms for configuring processing capabilities on processor 110.

It should be appreciated that although modules 111-115 are illustrated in FIG. 1 as being co-located within a single processing unit, in embodiments in which processor 110 includes multiple processing units, one or more of modules 111-115 may be located remotely from the other modules. The description of the functionality provided by the different modules 111-115 described herein is for illustrative purposes, and is not intended to be limiting, as any of modules 111-115 may provide more or less functionality than is described. For example, one or more of modules 111-115 may be eliminated, and some or all of its functionality may be incorporated, shared, integrated into, and/or otherwise provided by other ones of modules 111-115. Note that processor 110 may be configured to execute one or more additional modules that may perform some or all of the functionality attributed below to one of modules 111-115.

Control module 111 is configured to control operation of system 100, e.g. during a therapy session. Control module 111 is configured to control pressure generator 140 to adjust one or more levels of one or more parameters of the pressurized flow of breathable gas. Adjustments may be made in accordance with one or more of a (respiratory) therapy regimen, based on determined and/or obtained target pressures, based on one or more algorithms that control adjustments and/or changes in the pressurized flow of breathable gas, and/or based on other factors. Control module 111 is configured to control pressure generator 140 to provide the pressurized flow of breathable gas. Control module 111 may be configured to control pressure generator 140 such that one or more gas parameters of the pressurized flow of breathable gas are varied over time in accordance with a respiratory therapy regimen.

Adjustments by control module 111 may be made in an ongoing manner, for example at a particular sampling rate. The rate of adjustment may be 1 ms, 10 ms, 0.1 seconds, 0.5 second, 1 second, 2 seconds, 5 seconds, 10 seconds, 20 seconds, and/or another appropriate rate. Adjustments by control module 111 may be based on one or more subject-specific parameters and/or factors. In some embodiments, a user, e.g. subject 106, may provide one or more preferences or patient-specific information that may be taken into account by control module 111 during operation.

Parameter determination module 112 of system 100 in FIG. 1 is configured to determine one or more parameters related to a characteristic of the airways and/or lungs from output signals generated by sensor(s) 142. The one or more parameters may include one or more of breathing parameters, airway parameters, gas parameters, and/or other parameters from output signals generated by sensor(s) 142. These parameters are referred to individually as a respiratory parameter, and any combination of these parameters is referred to as respiratory parameters.

One or more gas parameters determined by parameter determination module 112 may be related to and/or derived from measurements of one or more of (peak) flow, flow rate, (tidal) volume, pressure, temperature, humidity, velocity, acceleration, gas composition (e.g. concentration(s) of one or more constituents), thermal energy dissipated, (intentional) gas leak, and/or other measurements related to the (pressurized) flow of breathable gas.

One or more breathing parameters determined by parameter determination module 112 may be related to and/or derived from gas parameters and/or other output signals conveying measurements of the pressurized flow of breathable gas. The one or more breathing parameters may include one or more of respiratory rate, breathing period, inhalation time or period, exhalation time or period, respiration flow curve shape, transition time from inhalation to exhalation and/or vice versa, transition time from peak inhalation flow rate to peak exhalation flow rate and/or vice versa, respiration pressure curve shape, maximum proximal pressure drop (per breathing cycle and/or phase), fraction of inspired oxygen, and/or other breathing parameters.

One or more airway parameters determined by parameter determination module 112 may be related to and/or derived from the generated output signals and/or other parameters derived therefrom. The one or more airway parameters may include one or more of lung impedance, airway resistance, airway reactance, and/or other airway parameters. Parameter determination module 112 may be configured to determine a monitoring parameter that reflects a change between a first measurement of a particular respiratory parameter and a second measurement of a particular respiratory parameter. The particular respiratory parameter may be lung impedance, airway resistance, and/or another respiratory parameter indicative of a characteristic of the lung and/or respiratory system.

The first measurement may be taken prior the second measurement. For example, the timing of the first and second measurement may be determined such that a change in lung impedance is caused by fluid shifting, settling and/or accumulating during a sleep session of subject 106. In some embodiments, the timing of the first and second measurement may be determined such that a change in lung impedance is caused by fluid dispersing and/or redistributing either during a non-sleeping period or after a sleep session of subject 106. The first and second measurements may be taken one or more minutes or hours apart. The first and second measurements may be taken on subsequent days, thus spanning a period of (mostly nocturnal) rest and/or sleep. In some embodiments, parameter determination module 112 may be configured to determine one or more differential impedance parameters indicative of lung impedance based on multiple measurements pertaining to the one or more generated output signals. For example, the one or more differential impedance parameters may include a parameter that reflects a differential within a span of 24 hours in an individual lung impedance parameter. The differential may be based on at least two measurements taken within the span of 24 hours.

In some embodiments, one or more airway parameters may be determined using a forced oscillation technique (FOT), which involves providing a known pressure waveform (interchangeably referred to as "forcing function") to the subject and interpreting the amplitude and phase relationship of the resulting airflow response of the subject. Forcing functions may include one or more of a series of impulses, step functions, sinusoids, and/or other functions or combinations thereof. By way of illustration, the use of a forced oscillation technique will be described using a simplified mathematical model of lung impedance (interchangeably referred to as an "airway and lung model"). More advanced mathematical models are considered within the scope of this disclosure. In the simplified model, the airway of a patient is represented by an effective resistance R, an effective inertance I, and an effective elastance E, combined in the following differential equation:

$$P(t) = I\frac{dQ(t)}{dt} + RQ(t) + E\int_0^t Q(t)\,dt + P_0$$

Note that Q(t) is the flow response to a sinusoidal pressure forcing function P(t) with frequency $f_{FOT}$ such that:

$$P(t) = P_p \sin(\omega t + \varphi)$$

Note that the angular frequency $\omega = 2\pi f_{FOT}$ and $\varphi$ equals the angular phase, which by convention can be assumed to be zero. Note that the disclosure is not intended to be limited in any way by this assumption, or by any other assumptions noted in this disclosure. The input impedance at the angular frequency may be given by:

$$Z(\omega) = R + j\left(\omega I - \frac{E}{\omega}\right)$$

The resonant angular frequency where the two reactances cancel each other out may be given by:

$$\omega_{res} = \sqrt{\frac{E}{I}}$$

Empirical data suggests that for an ordinary lung, the resonant frequency $f_{res}$ is between about 8 Hz and about 12 Hz, where $\omega_{res} = 2\pi f_{res}$. By selecting two frequencies at an adequate distance on either side of the resonant frequency, changes in both inertance and elastance may be tracked and/or monitored over time as a patient develops pulmonary edema and/or pulmonary congestion.

Assume two angular frequencies $\omega_1$ and $\omega_2$ on either side of the resonant frequency, such that the impedances are given by:

$$Z(\omega_1) = R(\omega_1) + jX(\omega_1) = R(\omega_1) + j\left(\omega_1 I - \frac{E}{\omega_1}\right), \text{ and}$$

$$Z(\omega_2) = R(\omega_2) + jX(\omega_2) = R(\omega_2) + j\left(\omega_2 I - \frac{E}{\omega_2}\right)$$

The measured values for $R(\omega)$ and $X(\omega)$ may be referred to as $R_m(\omega)$ and $X_m(\omega)$, respectively. Thus the following two equations hold:

$$X_m(\omega_1) = \omega_1 I - \frac{E}{\omega_1} \quad \text{Equation (A)}$$

$$X_m(\omega_2) = \omega_2 I - \frac{E}{\omega_2} \quad \text{Equation (B)}$$

For suitably chosen frequencies, equations (A) and (B) may be solved and E and I calculated. Specifically, $\omega_1$ and $\omega_2$ may be harmonically related to one another. For example, we can set $\omega_2 = 3\omega_1$. Via substitution:

$$X_m(\omega_2) = 3\omega_1 I - \frac{E}{3\omega_1} \quad \text{Equation (C)}$$

In some embodiments, equations (A) and (C) may be solved by measuring the total impedance magnitudes $|Z_{m1}|$ and $|Z_{m2}|$ and the respective phase angles $\theta_1$ and $\theta_2$ in a fast and efficient manner. For example, assuming zero phase for the pressure sinusoid, and assuming a sinusoidal pressure perturbation having an amplitude of $P_p$, for any given frequency $f_{FOT}$:

$$P(t) = P_p \sin(\omega t + 0°), \text{ where } \omega = 2\pi f_{FOT}$$

In phasor notation: $P_p \angle 0°$, and $Q_p \angle 0°$, wherein the flow has a phase angle $0°$. The measured impedance may be given by $$Z_m = \frac{P_p}{Q_p} \angle(-\theta°)$$

Ratio $$\frac{P_p}{Q_p}$$

may be calculated, determined, and/or estimated by monitoring the peak values of the pressure waveform and flow waveform and using cross correlation and/or coherence with respect to the forcing function vector. It is noted that approximations of this ratio may be sufficiently accurate, but possibly easier and/or faster to calculate, such as, by way of non-limiting example, $$\frac{P_{RMS}}{Q_{RMS}} \text{ or } \frac{P_{avg}}{Q_{avg}}.$$

The phase angle may be calculated, determined, and/or estimated by monitoring the average phase lag and/or lead between the pressure waveform and flow waveform. By way of non-limiting example, the phase angle θ may be determined by taking the inverse cosine of the cross-correlation coefficient between the pressure and flow vectors. The cross-correlation coefficient may be given by:

$$\cos(\theta) = \frac{P_p \cdot Q_p}{|P_p| \times |Q_p|}$$

where $P_p$ and $Q_p$ are the pressure and flow vectors respectively. A suitable window can be chosen for this calculation. In some embodiments, bias errors in the phase measurements may be reduced by dithering the forcing function. Once the magnitude and phase angle have been calculated, the impedance may be resolved into resistance and reactance. It is noted that lung impedance may be derived using different techniques and/or models. The examples provided above are not intended to limiting in any way.

By way of non-limiting example, impedance may be determined through other means. In some embodiments, a generalized complex forcing function $F_{forcing}(t)$ includes a linear superposition of N different frequencies, represented thus:

$$F_{forcing}(t) = \sum_{n=0}^{N} V_{p_n} e^{j(\omega_n t + \varphi_n)} \quad \text{equation (1)}$$

Note that $V_{p_n}$ is the amplitude of the $n^{th}$ component. In embodiments using a single complex function as forcing function, equation (1) reduces to:

$$F_{forcing}(t) = V_p e^{j(\omega t + \varphi)} \quad \text{equation (2)}$$

The "real" part of this forcing function may be represented by a set of coherent cycles of sampled (co)sine waves, e.g. stored in a table. This forcing function may be using to control the operation of pressure generator 140. For example, this forcing function may be used by perturbation module 115.

Using Fourier decomposition, the pressure and flow response waveforms are given by:

$$P(t) = \frac{a_{p_0}}{2} + a_{p_1} \cos\omega t + b_{p_1} \sin\omega t \quad \text{equation (3)}$$

$$Q(t) = \frac{a_{q_0}}{2} + a_{q_1} \cos\omega t + b_{q_1} \sin\omega t \quad \text{equation (4)}$$

Note that $a_{p_0}$ and $a_{q_0}$ represent the DC component, which may be due to one or more of noise, patient breathing, and/or other factors. The sine and cosine components are related to the forcing function. Note that higher order harmonics are ignored in equation (3) and (4) for sake of simplicity. This derivation is exemplary, and not intended to be limiting in any way. By reduction of equation (3) and (4):

$$P(t) = \frac{a_{p_0}}{2} + \text{Re}[(a_{p_1} + jb_{p_1})e^{j\omega t}] \quad \text{equation (5)}$$

$$Q(t) = \frac{a_{q_0}}{2} + \text{Re}[(a_{q_1} + jb_{q_1})e^{j\omega t}] \quad \text{equation (6)}$$

Equations (5) and (6) may be solved through several techniques, including but not limited to linear least squares minimization. In some embodiments, these equations may be solved in real-time.

Assuming P(t) and Q(t) are measured with a sampling period $T_s$, using at least W samples, W being three or more, equations (5) and (6) have the following discrete counterparts:

$$P_n = A \cdot X_{p_n}[n] \quad \text{equation (7)}$$

$$Q_n = A \cdot X_{q_n}[n] \quad \text{equation (8)}$$

Note that in equations (7) and (8):

$$P_n = \begin{bmatrix} P[n] \\ P[n+1] \\ \vdots \\ P[n+W-1] \end{bmatrix} \quad Q_n = \begin{bmatrix} Q[n] \\ Q[n+1] \\ \vdots \\ Q[n+W-1] \end{bmatrix}$$

$$A = \begin{bmatrix} 1 & \cos(\omega * 0 * T_s) & \sin(\omega * 0 * T_s) \\ 1 & \cos(\omega * 1 * T_s) & \sin(\omega * 1 * T_s) \\ \cdots & \cdots & \cdots \\ 1 & \cos(\omega * W * T_s) & \sin(\omega * W * T_s) \end{bmatrix}$$

$$X_{p_n}[n] = \begin{bmatrix} \frac{a_{p_0}[n+\frac{w}{2}]}{2} \\ a_{p_1}[n+\frac{w}{2}] \\ b_{p_1}[n+\frac{w}{2}] \end{bmatrix} \quad X_{q_n}[n] = \begin{bmatrix} \frac{a_{q_0}[n+\frac{w}{2}]}{2} \\ a_{q_1}[n+\frac{w}{2}] \\ b_{q_1}[n+\frac{w}{2}] \end{bmatrix}$$

By way of non-limiting example, some embodiments may solve these equations using a least squares minimization, which may produce a unique solution for sufficiently high values of W. Sufficiently high values of W may be greater than or equal to 3. By rearranging equations (7) and (8):

$$(A^T A) X_{p_n}[n] = A^T P_n \quad \text{equation (9)}$$

$$(A^T A) X_{q_n}[n] = A^T Q_n \quad \text{equation (10)}$$

By rearranging equations (9) and (10):

$$X_{p_n}[n] = (A^T A)^{-1} A^T P_n \quad \text{equation (11)}$$

$$X_{q_n}[n] = (A^T A)^{-1} A^T Q_n \quad \text{equation (12)}$$

By defining matrix B:

$$B = (A^T A)^{-1} A^T \quad \text{equation (13)}$$

Matrix B may be calculated. Matrix B may be constant for combinations of $T_s$ and W. Matrix B may be stored prior to operation of system 100. By substitution using matrix B:

$$X_{p_n}[n] = BP_n \quad \text{equation (14)}$$

$$X_{q_n}[n] = BQ_n \quad \text{equation (15)}$$

By solving equations (14) and (15) in real-time, the complex impedance may be calculated by dividing those components of the pressure and flow responses contributed exclusively by the forcing function, e.g. thusly:

$$Z_{RS}[n] = \frac{a_{p_1} - jb_{p_1}}{a_{q_1} - jb_{q_1}}$$

By repeating these steps for different frequencies, equations (A) and (B) may be solved.

Referring to FIG. 1, operation of parameter determination module 112 may be performed in an ongoing manner, for example at a particular sampling rate. The one or more respiratory parameters may be determined at different locations and/or positions within system 100 or near subject 106. In some embodiments, parameter determination module 112 may derive vectors of respiratory parameters in an ongoing manner during a period of monitoring subject 106. The vectors of the parameters may be based on vectors of generated output signals and/or other (vectors of) determined parameters.

Detection module 113 is configured to detect, monitor, and/or quantify a characteristic of a lung of the subject based on the monitoring parameter. Operation of detection module 113 may be based on one or more respiratory parameters and/or one or more generated output signals. In some embodiments, operation of detection module 113 may be based on one or more respiratory parameters related to lung impedance and/or airway resistance. In some embodiments, operation of detection module 113 may be based on a monitoring parameter that reflects a change in one or more measurements indicating lung impedance.

For example, the monitoring parameter may reflect a change in lung impedance between a first measurement taken before a sleep and/or resting period and a second measurement taken after the sleep and/or resting period. In some embodiments, the first measurement may be taken at or near the onset of a sleeping and/or resting period. In some embodiments, the second measurement may be taken at or near the end of a sleeping and/or resting period. The term "near" as used herein when referring to periods and/or durations may be interpreted as one or more minutes, about half an hour, about an hour, and/or another period. The monitoring parameter may reflect a change in measurements corresponding to one or more of pulmonary fluid shift, nocturnal fluid shift, daytime fluid shift, dispersal of pulmonary fluid during a particular period, and/or fluid shift spanning another period. The monitoring parameter may reflect a change in lung impedance across a night-time period, a day-time period, and/or another suitable part of the day.

In some embodiments, operation of detection module 113 may produce a diagnosis pertaining to pulmonary edema and/or pulmonary congestion. The diagnosis may include an identifier indicating confidence in and/or probability/likelihood of a correct diagnosis. In some embodiments, operation of detection module 113 may produce a quantification of the current status of the patient with regard to pulmonary edema and/or pulmonary congestion, the current status of the patient with regard to (nocturnal or daytime) fluid shift, and/or other quantifications. In some embodiments, detection module 113 may operate based on threshold for various parameters, such that specific predetermined actions are to be taken upon breaching a particular threshold. In some embodiments, detection module 113 may operate based on a change in status pertaining to one or more of a determined parameter, a produced diagnosis, and/or generally pertaining to the status of pulmonary edema and/or pulmonary congestion of subject 106.

In some embodiments, detection module 113 may be configured to determine whether a medical professional should be notified. Such a determination may be based on a change in status pertaining to pulmonary edema, airway resistance and/or pulmonary congestion of subject 106. In some embodiments, detection module 113 may be configured to issue and/or perform such notifications.

Trending module 114 is configured to detect trends in parameters. Detection may span one or more hours, one or more days, multiple days, one or more weeks, multiple weeks, one or more months, multiple months, and/or other periods. In some embodiments, trending module 114 may be configured to detect one or more trends in the monitoring parameter (determined by parameter determination module 112, as described above). For example, trending module 114 may be configured to detect one or more trends in the monitoring parameter, e.g. pertaining to nocturnal fluid shift, over a period of days, weeks, months, and/or other suitable periods. In some embodiments, detected trends by trending module 114 may be used by detection module 113 as a basis for operation. Trending module 114 may be configured to perform statistical operations and/or manipulations to produce results and/or detect trends. For example, trending module 114 may be configured to determine standard deviations and/or other statistical derivations for various parameters and/or values related to the operation of system 100.

In some embodiments, trending module 114 may be configured to detect trends in morning (i.e. post-sleeping period measurements) values of lung impedance, resistance, and/or reactance, in evening or night-time (i.e. pre-sleeping period measurements) values of lung impedance, resistance, and/or reactance. In some embodiments, trending module 114 may be configured to detect trends in values reflecting night-time accumulation of pulmonary fluid (e.g. based on a morning value minus a preceding night-time value), or values reflecting day-time dispersal and/or redistribution of pulmonary fluid (e.g. based on a night-time value minus a morning value measured on the same day).

Trending module 114 may be configured to monitor whether a change in one or more of the preceding values breaches a threshold pertaining to that type of value. For example, a monitored condition may be whether the night-time accumulation exceeds the (statistically expected) day-time dispersal by a predetermined margin. A monitored condition may be whether the statistically expected night-time accumulation exceeds the statistically expected day-time dispersal by a predetermined margin. A monitored condition may be whether the day-time dispersal is less, by at least a predetermined margin, than the statistically expected day-time dispersal. A monitored condition may be whether the night-time lung impedance measurement plus the statistically expected night-time accumulation is greater than the statistically expected morning lung impedance measurement by a predetermined margin. Additional arithmetic combinations of measured values, albeit morning or night-time, measured accumulation, measured dispersal, expected accumulation, expected dispersal, and/or derivative parameters are contemplated within the scope of this disclosure. Trending module 114 may operate based on lung impedance, respiratory reactance, airway resistance, other airway parameters, and/or any combination thereof.

Perturbation module 115 is configured to determine one or more perturbation parameters. Perturbation parameters define perturbations to be applied to the levels of one or more gas parameters of the pressurized flow of breathable gas. Perturbation parameters may define one or more aspects of perturbations, including, but not limited to, frequency, amplitude, duty cycle, selection of one or more applicable respiratory phases, and/or other aspects of perturbations to be applied to the levels of one or more gas parameters of the pressurized flow of breathable gas. In some embodiments, perturbations may represent a forcing function. For example, a forcing function may be used to determine, by way of non-limiting example, lung impedance. An example of using a forcing function is described above, with reference to forced oscillation technique. In some embodiments, the one or more perturbation parameters may define the amplitude and frequency of a sinusoidal pressure forcing function P(t). In some embodiments, control module 111 is configured such that the levels of the one or more gas parameters of the pressurized flow of breathable gas include the perturbations defined by perturbation module 115.

One or more perturbation parameters may be automatically adjusted and/or determined. In some embodiments, one or more perturbation parameters may be automatically adjusted and/or determined based on one or more output signals generated by one or more sensors 142. For example, one or more outputs signals (or parameters derived therefrom), may form the basis for a determination and/or adjustment of one or more perturbation parameters. In some embodiments, applying perturbations—by perturbation module 115 in conjunction with other modules of system 100—may be responsive to a determination that a level of lung impedance has breached a threshold level.

Perturbation module 115 may be configured such that one of the perturbation parameters includes a range of frequencies of perturbations to be applied. The range may be, e.g., from about 2 Hz to about 15 Hz, from about 8 Hz to about 12 Hz, and/or another range of frequencies. In some embodiments, perturbation module 115 may gradually, e.g. across multiple respiratory cycles, sweep through the range of frequencies of perturbations to be applied. Other ways to determine a frequency of perturbations within the range of frequencies, including a determination according to one or more predetermined patterns, are contemplated.

Determinations by parameter determination module 112 may be based on the perturbation parameters determined by perturbation module 115. For example, detection of the start of an inhalation or exhalation (sometimes referred to as triggering or cycling) may take perturbations and/or perturbation parameters into account. Some or all of this functionality may be incorporated or integrated into other computer program modules of system 100.

Figure 2:
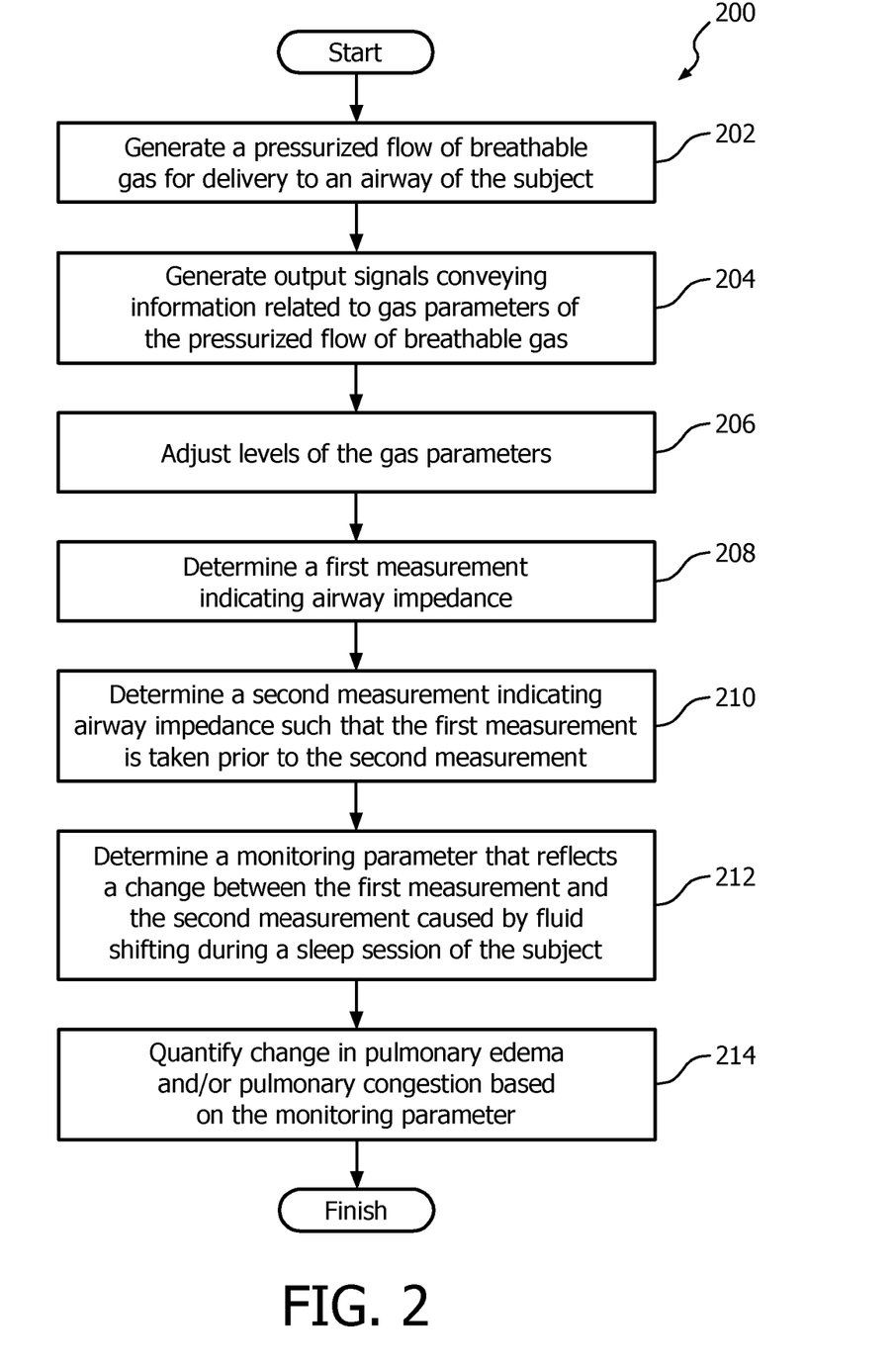
FIG. 2 illustrates a method to monitor pulmonary edema and/or pulmonary congestion, according to one or more embodiments.

FIG. 2 illustrates a method 200 for monitoring pulmonary edema and/or pulmonary congestion. The operations of method 200 presented below are intended to be illustrative. In certain embodiments, method 200 may be accomplished with one or more additional operations not described, and/or without one or more of the operations discussed. Additionally, the order in which the operations of method 200 are illustrated in FIG. 2 and described below is not intended to be limiting.

In certain embodiments, method 200 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

At an operation 202, a pressurized flow of breathable gas is generated for delivery to the airway of a subject. In some embodiments, operation 202 is performed by a pressure generator the same as or similar to pressure generator 140 (shown in FIG. 1 and described herein).

At an operation 204, one or more output signals are generated, the one or more output signals conveying information related to one or more gas parameters of the pressurized flow of breathable gas. In some embodiments, operation 204 is performed by one or more sensors the same as or similar to the one or more sensors 142 (shown in FIG. 1 and described herein).

At an operation 206, one or more levels are adjusted of the one or more gas parameters of the pressurized flow of breathable gas. In some embodiments, operation 206 is performed by a control module the same as or similar to control module 111 (shown in FIG. 1 and described herein).

At an operation 208, a first measurement is determined indicating lung impedance of the subject, wherein the first measurement is based on the one or more generated output signals. In some embodiments, operation 208 is performed by a parameter determination module the same as or similar to parameter determination module 112 (shown in FIG. 1 and described herein).

At an operation 210, a second measurement is determined indicating lung impedance of the subject, wherein the second measurement is based on the one or more generated output signals. The first measurement is taken prior to the second measurement. In some embodiments, the timing of the first measurement and the second measurement, e.g. with respect to a sleeping session of the subject, results in a change and/or allows for an observed and/or observable change in the lung impedance between the first measurement and the second measurement including a change in the lung impedance caused by fluid shifting, settling, and/or accumulating during the sleep session of the subject. In some embodiments, operation 210 is performed by a parameter determination module 112 the same as or similar to parameter determination module 112 (shown in FIG. 1 and described herein).

At an operation 212, a monitoring parameter is determined that reflects the change between the first measurement and the second measurement. In some embodiments, operation 212 is performed by a parameter determination module the same as or similar to parameter determination module 112 (shown in FIG. 1 and described herein).

At an operation 214, change in pulmonary edema, airway resistance and/or pulmonary congestion is quantified and/or detected based on the monitoring parameter. In some embodiments, operation 214 is performed by a detection module the same as or similar to detection module 113 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although this description includes details for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that, to the extent possible, one or more features of any embodiment are contemplated to be combined with one or more features of any other embodiment.

What is claimed is:

1. A method for detecting lung characteristics with a system, the system comprising a pressure generator, one or more sensors, and one or more processors, the method comprising:

receiving, from the one or more sensors, one or more output signals conveying information related to one or more gas parameters of pressurized flow of breathable gas from the pressure generator delivered to an airway of a subject;

performing a first perturbation at a first frequency which is less than a resonant frequency of the lung and a second perturbation at a second frequency which is more than the resonant frequency of the lung, via the pressure generator, to the one or more gas parameters of the pressurized flow of breathable gas;

determining a first lung impedance based on first output signals collected during the first perturbation, the first output signals collected, via the one or more sensors, before a sleep session;

determining a second lung impedance based on a second output signals collected during the second perturbation, the second output signals collected, via the one or more sensors, after the sleep session;

determining a change between the first lung impedance and the second lung impedance; and determining the characteristic of the lung of the subject based on the change in the lung impedance, wherein the characteristic includes pulmonary edema and/or pulmonary congestion, wherein the first and the second lung impedances are determined using an airway and lung model that establishes a relationship between parameters related to the airway, the lung, and the first perturbation and the second perturbation performed by the pressure generator, wherein the parameters related to the airway of the airway and lung model include an effective resistance R, an effective inertance I, and an effective elastance E.

2. The method of claim 1, further comprising automatically adjusting the first perturbation and/or the second perturbation based on the change breaching a predetermined threshold.

3. The method of claim 1, wherein the first frequency less than the resonant frequency and (ii) the second frequency greater than the resonant frequency are each a given distance on a respective side of the resonant frequency to enable tracking and/or monitoring of changes in both the effective inertance and effective elastance over time.

4. The method of claim 3, wherein the first perturbation frequency and the second perturbation frequency are harmonically related to one another.

5. The method of claim 1, wherein the one or more processors are further configured to (i) obtain sensor-generated output signals associated with one or more further measurements subsequent to the second output signals, (ii) determine lung impedance values based on the one or more further measurements, and (iii) determine a trend in the lung impedance values, the trend being caused by day-time disposal and/or redistribution of pulmonary fluid.

6. The method of claim 1, wherein the first and/or the second perturbation comprises one or more perturbation parameters including at least an amplitude and frequency of a sinusoidal pressure function.

7. The method of claim 1, wherein the first perturbation and the second perturbation represent a forcing function used to determine the first lung impedance and the second lung impedance.

8. The method of claim 1, wherein the parameters related to the airway and the lung include an airway resistance, an elastance, and an inertance.

* * * * *